(12) United States Patent
Carroll et al.

(10) Patent No.: US 6,404,854 B1
(45) Date of Patent: Jun. 11, 2002

(54) DENTAL X-RAY IMAGING SYSTEM

(75) Inventors: Seamus Carroll, Cold Spring, NY (US); Christer Fröjdh, Sundsvall (SE)

(73) Assignee: AFP Imaging Corporation, Elmsford, NY (US)

( * ) Notice: Subject to any disclaimer, the term of this patent is extended or adjusted under 35 U.S.C. 154(b) by 0 days.

(21) Appl. No.: 09/711,798

(22) Filed: Nov. 13, 2000

Related U.S. Application Data

(63) Continuation-in-part of application No. 09/603,395, filed on Jun. 26, 2000.

(51) Int. Cl.[7] .................................................. H05G 1/64
(52) U.S. Cl. ........................................ 378/98.8; 378/98
(58) Field of Search ............ 378/98.8, 98; 250/370.09, 250/370.11; 348/241, 250, 301

(56) References Cited

U.S. PATENT DOCUMENTS

| | | | |
|---|---|---|---|
| 4,160,997 A | 7/1979 | Schwartz | 358/93 |
| 4,593,400 A | 6/1986 | Mouyen | 378/99 |
| 5,220,170 A | 6/1993 | Cox et al. | 250/370.09 |
| 5,331,166 A | 7/1994 | Yamamoto et al. | 250/370.11 |
| 5,391,881 A | 2/1995 | Jeuch et al. | 250/370.09 |
| 5,434,418 A | 7/1995 | Schick | 250/370.11 |
| 5,440,130 A | 8/1995 | Cox et al. | 250/370.09 |
| 5,444,756 A | 8/1995 | Pai et al. | 378/98.8 |
| 5,454,022 A | 9/1995 | Lee et al. | 378/98.8 |
| 5,510,623 A | 4/1996 | Sayag et al. | 250/370.11 |
| 5,513,252 A | 4/1996 | Blaschka et al. | 250/394 |
| 5,514,873 A | 5/1996 | Schulze-Ganzlin et al. | 250/394 |
| 5,519,437 A | 5/1996 | Nelvig | 348/162 |
| 5,528,043 A | 6/1996 | Spivey et al. | 250/370.09 |
| 5,572,566 A | 11/1996 | Suzuki et al. | 378/98.2 |
| 5,579,361 A | 11/1996 | Augais et al. | 378/38 |
| 5,668,378 A * | 9/1997 | Petrick et al. | 250/370.09 |
| 5,671,738 A | 9/1997 | Thörnberg | 128/653.1 |
| 5,677,537 A | 10/1997 | Pfeiffer | 250/370.09 |
| 5,677,940 A | 10/1997 | Suzuki et al. | 378/38 |
| 5,693,948 A | 12/1997 | Sayed et al. | 250/370.09 |

(List continued on next page.)

Primary Examiner—Robert H. Kim
Assistant Examiner—Irakli Kiknadze
(74) Attorney, Agent, or Firm—Cooper & Dunham LLP

(57) ABSTRACT

An X-ray imaging system comprising an X-ray image sensor and an image capture controller is provided. The X-ray image sensor includes a sensor array comprising a plurality of CMOS active column sensors. The image capture controller communicates with the X-ray image sensor to read out pixel values from selected ones of the CMOS active column sensor elements. The image capture controller may randomly select reference pixels from the plurality of CMOS active column sensor elements, and compare a signal of the reference pixels to a predetermined level to determine a start of X-ray exposure. The image capture controller also may randomly select second reference pixels from the plurality of CMOS active column sensor elements, and monitor the second reference pixels to determine an end of X-ray exposure. The X-ray imaging system also may include a wireless interface for coupling the X-ray image sensor to the image capture controller. The X-ray imaging system may be used as a dental X-ray imaging system. An intraoral X-ray image sensor comprising a scintillator that converts an X-ray energy image into a visible-light image and a sensor array including a plurality of CMOS active column sensors which converts the visible-light image into an electrical signal also may be provided.

16 Claims, 9 Drawing Sheets

U.S. PATENT DOCUMENTS

| | | | |
|---|---|---|---|
| 5,694,448 A | 12/1997 | Morcom | 378/98.8 |
| 5,744,806 A | 4/1998 | Fröjd | 250/370.09 |
| 5,852,296 A * | 12/1998 | Tsukamoto et al. | 250/370.09 |
| 5,894,129 A | 4/1999 | Pool | 250/370.09 |
| 5,912,942 A | 6/1999 | Schick et al. | 378/98.8 |
| 6,002,742 A | 12/1999 | Nelvig | 378/98.8 |
| 6,021,172 A | 2/2000 | Fossum et al. | 377/60 |
| 6,067,113 A * | 5/2000 | Hurwitz et al. | 348/241 |
| 6,069,935 A | 5/2000 | Schick et al. | 378/98.8 |
| 6,084,229 A | 6/2000 | Pace et al. | 250/208.1 |
| 6,118,482 A * | 9/2000 | Clark et al. | 348/308 |
| 6,163,029 A * | 12/2000 | Yamada et al. | 250/370.09 |
| 6,166,768 A * | 12/2000 | Fossum et al. | 348/308 |
| 6,201,573 B1 * | 3/2001 | Muzuno | 348/308 |
| 6,219,401 B1 * | 4/2001 | Tachibana et al. | 378/39 |
| 6,243,441 B1 * | 6/2001 | Zur | 378/98.8 |

* cited by examiner

FIG. 1
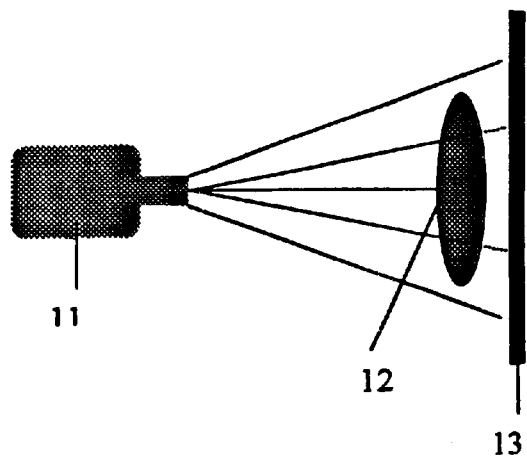
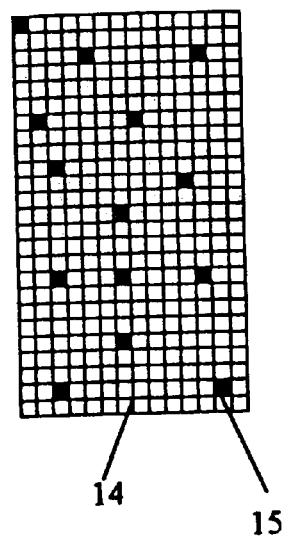
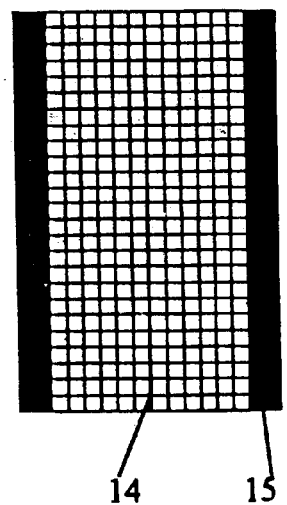
FIG. 2A     FIG. 2B

DENTAL X-RAY IMAGING SYSTEM

CROSS REFERENCE TO RELATED APPLICATION

This application is a continuation-in-part of U.S. patent application Ser. No. 09/603,395, filed Jun. 26, 2000, and entitled "TRIGGERING OF SOLID STATE X-RAY IMAGERS WITH NON-DESTRUCTIVE READOUT CAPABILITY".

FIELD OF THE INVENTION

The present invention relates to an X-ray imaging system. In particular, the invention relates to a system of dental X-ray imaging using a complementary metal oxide semiconductor active column sensor adapted for X-ray imaging.

BACKGROUND OF THE INVENTION

An active pixel is a semiconductor device capable of converting an optical image into an electronic signal. Active pixels can be arranged in a matrix and utilized to generate video signals for video cameras, still photography, or anywhere incident radiation needs to be quantified. When incident radiation interacts with a photosite, charge carriers are liberated and can be collected for sensing. The number of carriers collected in a photosite represents the amount of incident light impinging on the site in a given time period.

There are two basic devices, i.e., photodiodes and photogates, with many variants, employed to collect and sense, charge carriers in a photosite. Variants of photodiodes include Pinned, P-I-N, Metal-Semiconductor, Heterojunction, and Avalanche. Photogate structures include: Charge Coupled Devices (CCD), Charge Injection Devices (CID), and variants that include virtual phase, buried channel and other variations that utilize selective dopants which are used to control charge collection and transfer underneath and between the photogate(s) and the sense node.

Solid state imagers heretofore used have been dominated by CCDs because of their low noise as compared to photodiodes and CIDs. However, the low noise of the CCD requires the imager to be read in a fixed format and once the charge is read it is destroyed.

Solid state imaging devices have developed in parallel with CMOS technology and as a result proprietary processes have been developed to maximize imager performance characteristics and wafer yield. Coupling the collected photon charge from the pixel to the periphery amplifier typically requires proprietary processing steps not compatible with industry standard CMOS (complementary metal oxide semiconductor) or BiCMOS (bipolar CMOS) processes. There has been a movement to transfer the proprietary processes to an industry standard CMOS process which provides advantages such as competitive wafer processing pricing, and on chip timing, control and processing electronics.

A CMOS compatible, CID imager has been fabricated. The imager could either be operated as a random access CID, or all the columns could be summed together and operated as a linear active pixel sensor. The imager has a preamplifier and correlated double sampling (CDS) circuit per column. The CDS circuit stores the initial value of each pixel before each frame is captured, which indicates the offset compared to true black, i.e., zero incident light. After the frame is captured, each pixel's value is adjusted up or down based on that initial value.

U.S. Pat. No. 5,471,515 describes area arrays utilizing active pixel sensors in which a photodiode or photogate is coupled to an output source follower amplifier which in turn drives a CDS circuit. Two outputs of the CDS cell then drive two more source followers circuits that in turn are fed into a differential amplifier. The source follower circuits typically have gains less than unity that vary from one source follower to another. The source follower gain variation is due to variations of FET thresholds, and results in a pixel to pixel gain mismatch. Also, the active pixel sensors suffer gain variations due to the CDS circuit per column, when the CDS employs a source follower pair to drive its output. The resulting CDS signal and its corresponding offset can have different gains that are not correctable by the differential amplifier. Also, the source follower configuration of active pixels does not allow for binning of pixels, i.e., summation of two or more pixel signals at once.

CMOS image sensors now also are available. The CMOS image sensor is an integrated circuit (IC) that detects and converts incident light (photons) into electronic charge (electrons) through a photoconversion process. The sensor includes an array of photodiodes that can detect light in the visible spectrum. CMOS transistors in each pixel select, amplify and transfer the photodiode signals. A CMOS imager or imaging system may include both the sensor and supporting circuitry for further amplifying and processing the detected image. CMOS imagers offer several significant advantages over CCD imagers, including lower overall cost, lower power requirements and a higher level of integration that can reduce the size of the imaging system. In addition, CMOS imagers are relatively easy to manufacture in standard CMOS wafer fabrication facilities. Most CMOS imagers today use Active Pixel Sensor (APS) technology, which utilizes an amplifier for each pixel. Each of those amplifiers requires at least three field effect transistors (FET) to implement. Due to process variations during the manufacture of these amplifiers, the actual gain and offset of each amplifier is slightly different from those of the other amplifiers. As a result, APS imagers suffer from high fixed pattern noise (FPN) problems. The resulting video can appear as if viewed through a dirty, scratchy window.

Some APS systems counteract the gain and offset issues by creating tables of multiplier and offset values to correct the incoming video. As long as the temperature remains relatively constant, these tables can be used with little or no modification. However, the tables add to the complexity of the system.

A solution to the variation in gain from one amplifier to another is to implement a unity gain amplifier (UGA) for every pixel. Each UGA requires, however, the use of at least six FETs, which increases the complexity of the product significantly. In addition, each FET decreases the active area of the corresponding pixel. With six or more FETs per pixel, the active area is greatly reduced. Further, the added complexity raises the cost of the product, which eliminates one of the major advantages that CMOS technology is intended to provide.

Electronic image sensors, such as CCD or CMOS pixel sensors, have been adapted to be X-ray sensitive elements in dental and medical applications. The digital X-ray sensor is used to detect and record X-ray images which typically are downloaded to a personal computer via a cable. Examples of use of CCD-type and other X-ray image sensors in dental and/or medical environments are described in U.S. Pat. Nos. 5,671,738 and 5,744,806, which are incorporated herein by reference. An X-ray detector that comprises a plurality of CMOS active pixel sensors is described in U.S. Pat. Nos. 5,912,942 and 6,069,935.

As discussed above, CCD sensors and CMOS active pixel sensors, however, have their disadvantages.

SUMMARY OF THE INVENTION

The present invention provides an X-ray imaging system comprising, in accordance with one embodiment, an X-ray image sensor including a plurality of CMOS active column sensor elements, and image capture controller communicating with the X-ray image sensor to read out pixel values from selected ones of the plurality of CMOS active column sensor elements of the X-ray image sensor. The image capture controller randomly may select reference pixels from the plurality of CMOS active column sensor elements, and compare a signal of the reference pixels to a predetermined level to determine a start of X-ray exposure. The image capture controller also may randomly select second reference pixels from the plurality of CMOS active column sensor elements, and monitor the second reference pixels to determine and end of X-ray exposure.

The X-ray imaging system also may include a wireless interface for coupling the X-ray image sensor to the image capture controller.

The X-ray imaging system may be used as a dental X-ray imaging system.

The present invention also provide an intraoral X-ray image sensor comprising, in accordance with one embodiment, a scintillator that converts an X-ray energy image into a visible-light image, and a sensor array including a plurality of CMOS active column sensors, said sensor array converting the visible-light image into an electrical signal.

BRIEF DESCRIPTION OF THE DRAWINGS

The above and numerous other objectives, features and advantages that may be achieved by the present invention would be more readily understood from the following detailed description by referring to the accompanying drawings wherein:

FIG. 1 shows a schematic view of an X-ray imaging system;

FIG. 2A shows a schematic view of selected reference pixels in accordance with one embodiment of the present invention;

FIG. 2B shows a schematic view of selected reference pixels in accordance with another embodiment of the present invention;

DETAILED DESCRIPTION OF THE INVENTION

Figure 3:
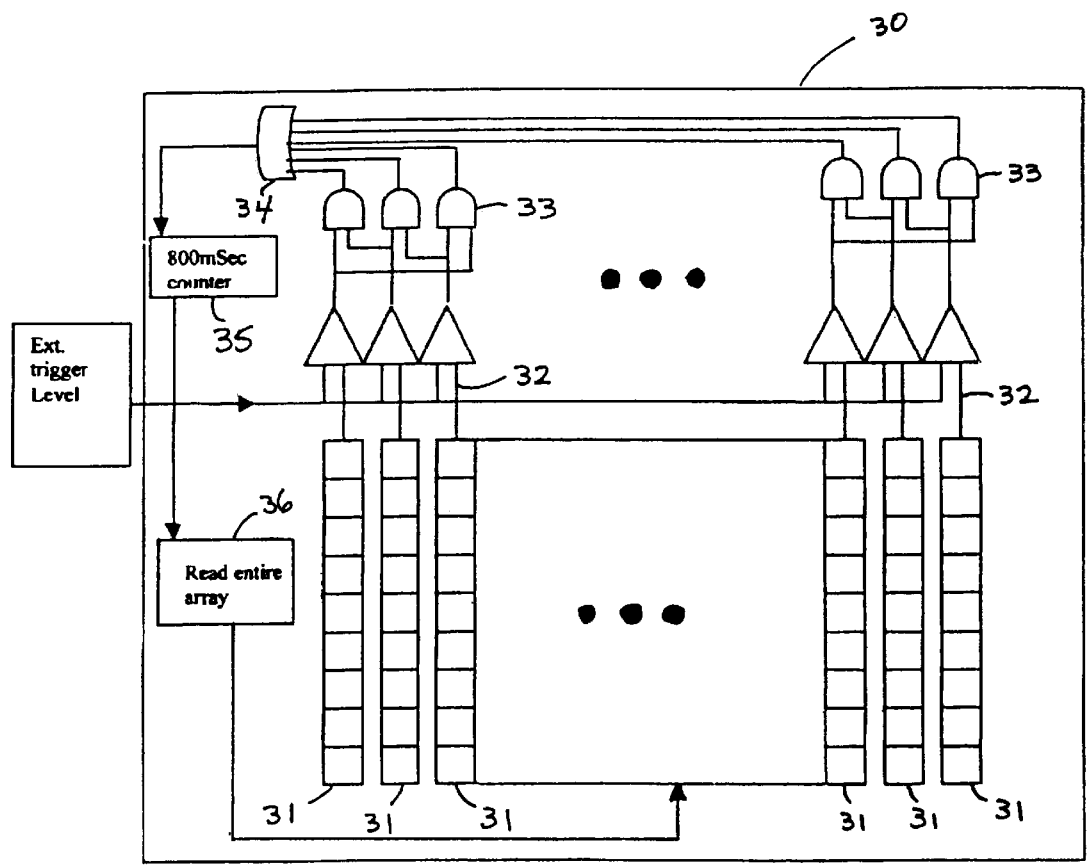
FIG. 3 shows a schematic view of means for image capture in an X-ray image sensor in accordance with an embodiment of the present invention.

To explain the invention, some embodiments are described in connection with the drawings and their supporting descriptions provided below.

FIG. 1 shows an X-ray imaging system 1 with an X-ray generator 11 emitting X-rays. The X-ray source 11 is arranged to irradiate an object to be imaged 12. Part of the X-rays are absorbed by the object to be imaged 12. An X-ray image sensor 13 is located behind that object. The X-ray photons which pass through the object are detected by the image sensor 13.

Sensor 13 preferably is an active column sensor adapted for X-ray imaging. An active column sensor (ACS) is described in U.S. Pat. No. 6,084,229, which is incorporated herein by reference. The ACS includes a photosensitive device such as a photodiode or photogate having a sense node coupled to an FET located adjacent to the photosensitive region. Another FET, forming a differential input pair of an operational amplifier, is located outside of the array of pixels. The operational amplifier may be configured for unity gain and a row or column of input FETs is connected in parallel. A correlated double sampler may be connected to the output of the operational amplifier for providing a fixed pattern noise free signal. The ACS embodies the recognition that all but one of the FETs (the input FET) of each UGA for each pixel of a column in a CMOS active pixel sensor are redundant. In the ACS, these redundant FETs are absent, and replaced with a single shared UGA amplifier at each column. The ACS has one dual input FET per pixel, and four or so shared FETs at each column, i.e., a shared UGA for all the pixels in a column. The ACS has low noise level, random access, and uniform gain and response from the pixels. The ACS also may have binning.

Figure 7A:
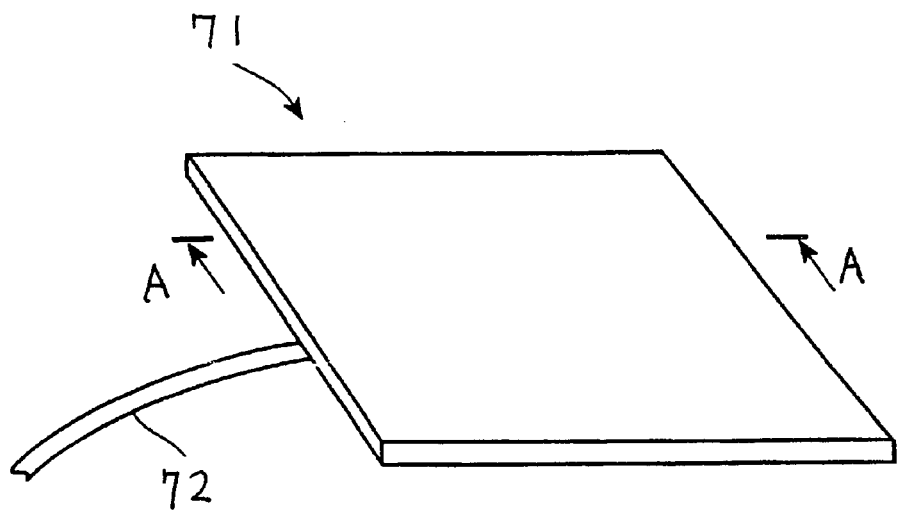
FIG. 7A shows a perspective view of an active column sensor X-ray detector, in accordance with one embodiment of the present invention.

FIG. 7A depicts one embodiment of an ACS X-ray detector, in a very general manner. The detector 71 is connected to a cable 72 which transmits electrical signals generated by the X-ray detector to a computer. As discussed further below, peripheral processing may be performed by the computer or by circuitry coupled to the computer.

Figure 7B:
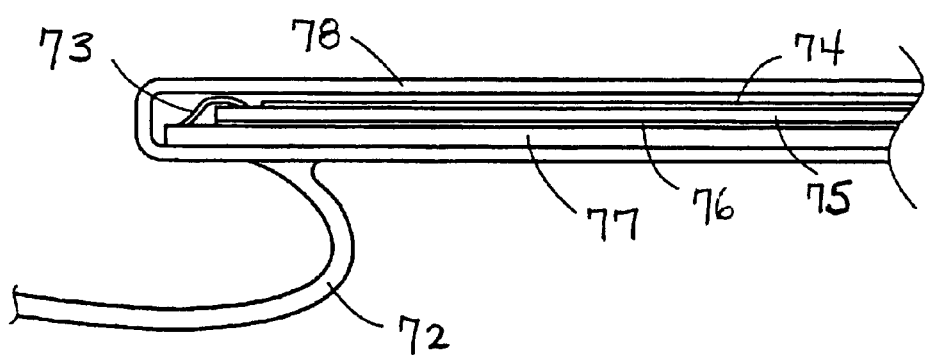
FIG. 7B shows a cross-sectional view taken along section line A—A of the active column sensor X-ray detector shown in FIG. 7A.

FIG. 7B is a magnified cross sectional view of an embodiment of the X-ray detector of FIG. 7A, taken from section line A—A. In the embodiment shown in FIG. 7B, the X-ray detector includes a scintillator 74 on top of a semiconductor 75, all supported on a passivated ceramic substrate 77. In general terms, the scintillator 74 converts X-rays into visible light while the semiconductor 75, in turn, converts the light into electrical signals representing the image.

The scintillator layer 74 is interposed between the X-ray source and the semiconductor layer 75, to both protect the semiconductor from unwanted X-ray exposure and to provide conversion of the X-rays to visible light for direct detection by the semiconductor. X-ray-to-light converting materials that may be used for the scintillator include gadolinium oxysulphide, cesium iodide, cadmium tungstate, cadmium telluride, cadmium sulfide, calcium tungstate, zinc sulfide and zinc cadmium sulfide. Scintillating glass, such as for example terbium glass, or scintillating optical fibers also may be used. The scintillator 74 is positioned to be directly exposed to the X-rays which readily pass through a protective enclosure 78.

The semiconductor 75 comprises an array of ACS pixels and an integrated signal amplifier. The electrical signals produced by the semiconductor 75 are conveyed to the cable 72 via conductive lead 73. The conductive lead 73 also may convey electrical power and control signals from the computer to the semiconductor 75.

The semiconductor 75 may sit on top of an X-ray absorption layer 76. Absorption layer 76 absorbs any X-rays which are not converted by the scintillator 74, to prevent those X-rays from hitting the patient, and absorbs any backscattered radiation. X-ray absorbing materials that may be used for layer 76 include, for example, lead and tungsten.

The entire X-ray detector is enclosed in protective enclosure 78, which protects the X-ray detector from shock and moisture, while being permeable to X-ray radiation. Protective enclosure 78 may be made from, for example, aluminum or any one of many formulations of plastic known in the art. The side of the sensor that should be exposed to the X-rays and the actual size of the imaging area may be identified on the sensor capsule 78, so that proper positioning of the sensor would be apparent to the user. If the cable is connected to the back of the sensor (as shown in FIG. 7B) instead of end of the sensor, proper positioning of the sensor likely would be more apparent to the user.

The system 1 may be used in assorted digital X-ray imaging applications, including digital dental X-ray imaging to display and record dental radiographic images using a conventional dental X-ray source and a computer. The digital X-ray imaging system may include hardware and software components.

Figure 8A:
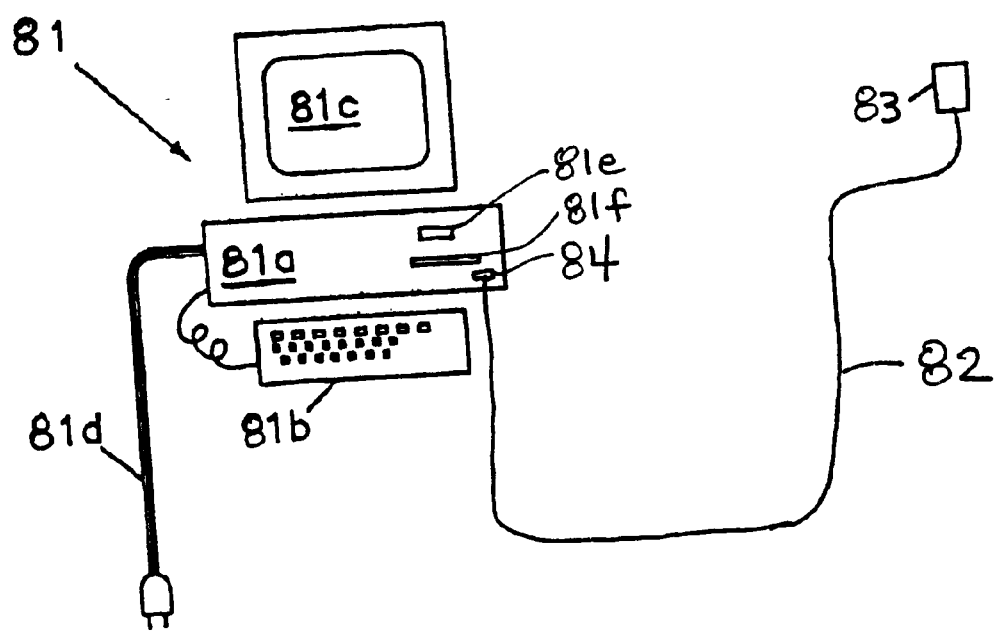
FIG. 8A shows a schematic view of some hardware components in a dental X-ray imaging system, in accordance with one embodiment of the present invention.
Figure 8B:
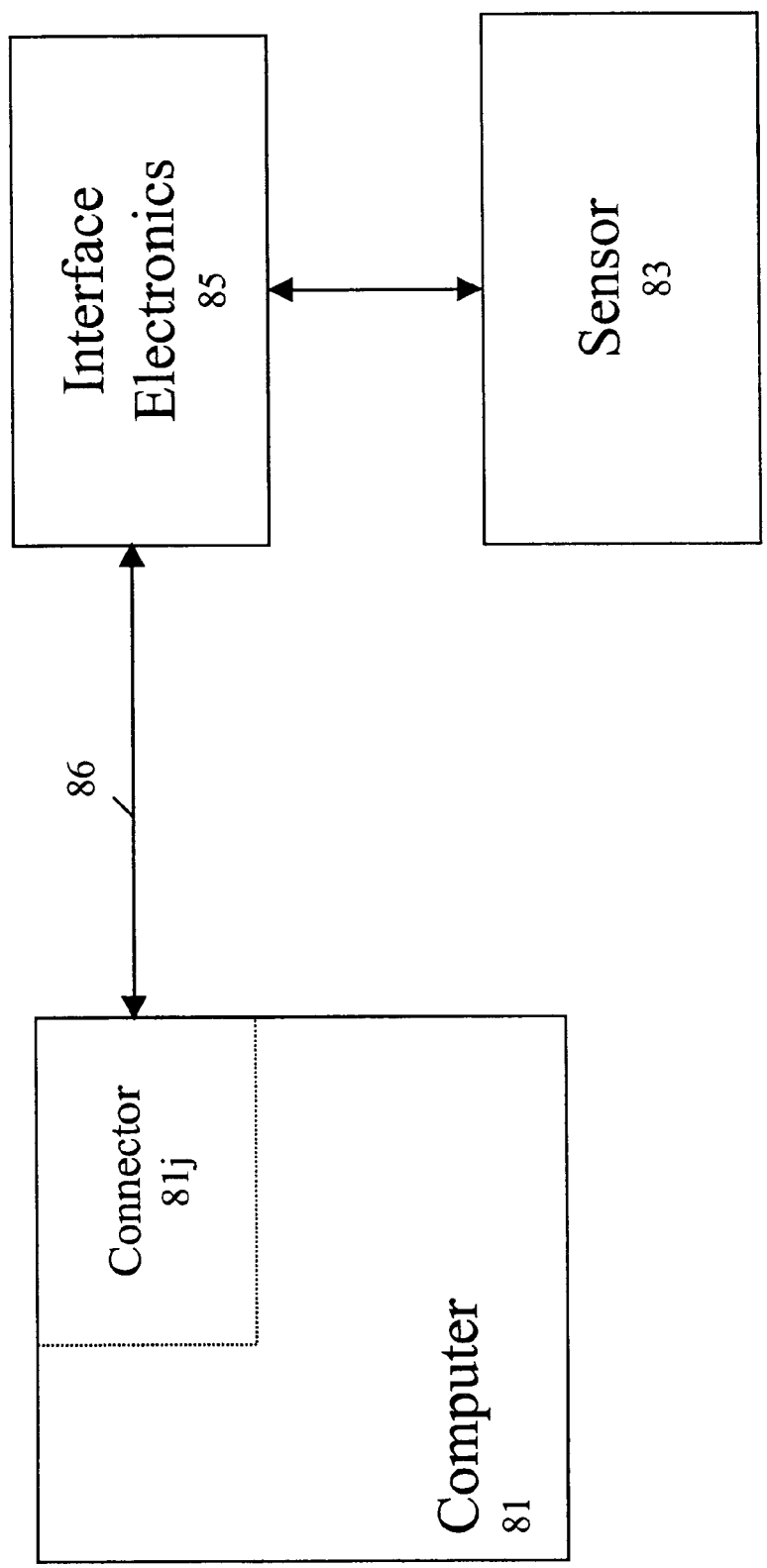
FIG. 8B shows a block diagram of some hardware components in a dental X-ray imaging system, in accordance with another embodiment.

FIGS. 8A and 8B show some of the hardware components that may be included in the system. The hardware components may comprise ACS image sensor 83, and interface electronics and connector 84 for interface to computer 81. These components may be linked together by a cable 82.

Sensors of different sizes may be provided. In a dental application, a sensor that may be inserted into the patient's mouth preferably is provided. In one exemplary embodiment for a dental application, two sensors, having the approximate dimensions of 42 mm×30 mm×5 mm and 34 mm×25 mm×5 mm, respectively, are provided. Dimensions different from these exemplary dimensions may be selected, according to application and/or to accommodate an ergonomic or stylistic design. Image sensor 83 may be inserted into the patient's mouth and positioned to record the radiographic image of the teeth. The sensor may be connected to the computer via cable 82 with, for example, a standard USB computer interface in one embodiment.

Interface electronics and connector 84, in the embodiment shown in FIG. 8A, are integrated with the packaging of computer 81. The user may unplug the sensor at the connector to switch to alternate sensor assemblies.

In another embodiment (FIG. 8B), there is an intermediate connection point 85 between sensor 83 and computer 81. Interface electronics 85 is connected to computer 81 via a standard-type, e.g., USB (Universal Serial Bus), cable/connector 86. While the user could disconnect the sensor from the computer by detaching the (e.g., USB) cable/connector from a USB port 81j of the computer if desired, USB connectors usually are provided on the back of the computer and therefore may be inconvenient to access. In addition, many low cost computers use low quality USB connectors which may fail in as little as one hundred (or even less) connection cycles. Thus, it is desirable to leave the USB cable connected to the computer and have a high reliability connector 85 to connect the sensor to the cable 86. Interface 85 may be, for example, a high reliability USB interface or a FireWire. Interface 85 may comprise a pair of mating connectors which may be detachable or permanently attached.

The interface electronics and connector optionally also may include a wireless interface for communicating with the image sensor 83 through a wireless communication link. One of a number of wireless interfaces, such as for an infrared optical link or radio frequency (e.g., spread spectrum RF) link, known in the art may be used. In such an embodiment, the X-ray image sensor also is provided with a wireless interface.

The wireless sensor may have, in one embodiment, a rechargeable battery for powering the sensor, which is placed in a recharger between uses. In another embodiment, the sensor has a capacitor which, instead of or along with a battery, stores the energy. When the sensor is removed from the charger and placed in the patient's mouth, the X-rays would trigger the sensor and discharge the capacitor, while one or more images would be held in memory on the sensor. Then, the sensor may be placed into a charger cradle. Other charge storage devices that are able to provide the power required by the sensor may be integrated with the wireless sensor. Each of the charge storage devices described above may be charged by the recharger through direct electrical connection or by inductive charging (see, e.g., U.S. Pat. No. 5,959,433). The charger cradle also may function as a data download station. When the image data is downloaded, the sensor is cleared and the charge storage device is recharged for the next use.

Figure 9:
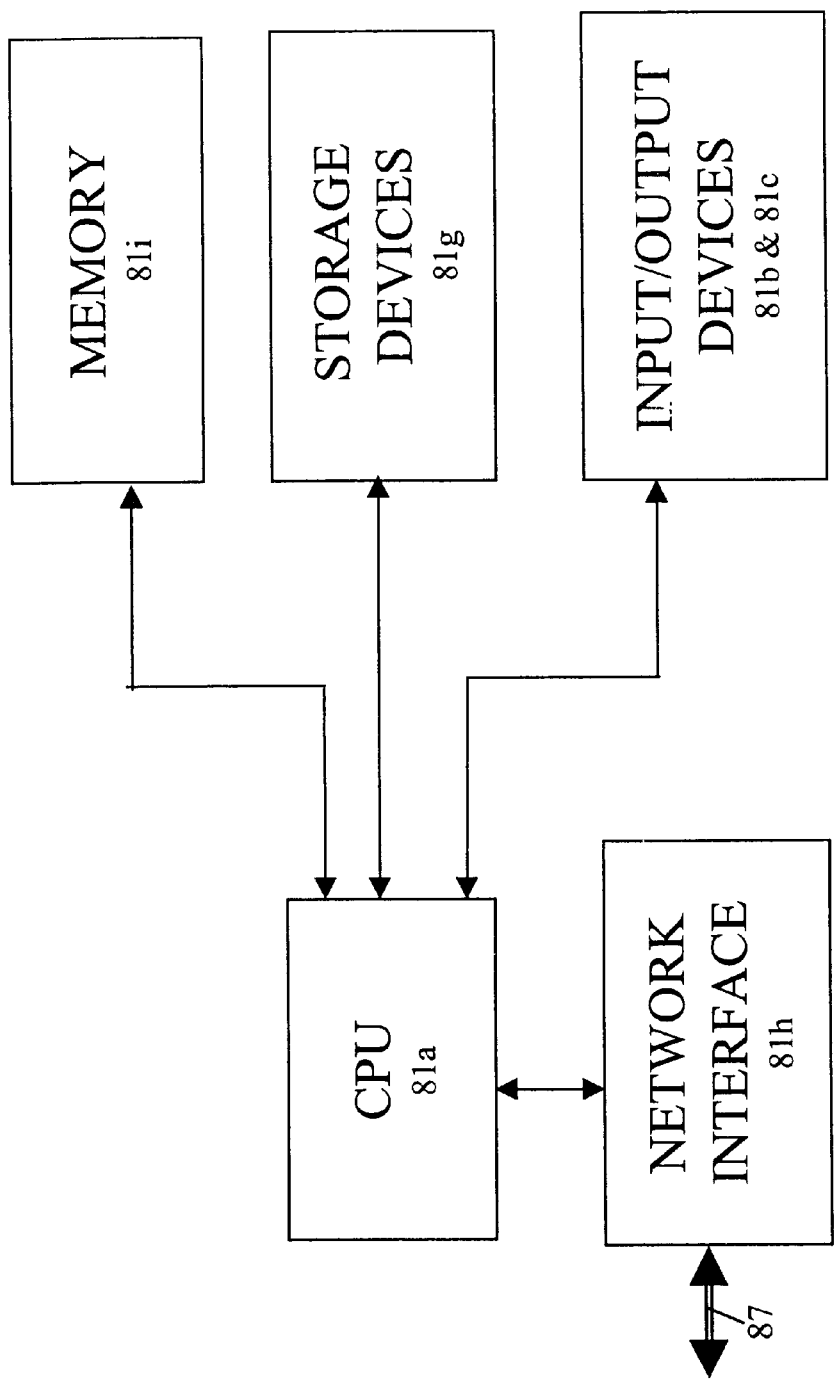
FIG. 9 shows a block diagram of a computer which may be used in the dental X-ray imaging systems shown in FIGS. 8A and 8B.

Computer 81 typically is a personal computer and may have the components shown in FIGS. 8 and 9. As one skilled in the art would appreciate, computer 81, alternatively, may be another computing device, such as a computer workstation, a notebook computer, or a handheld computer, e.g., personal digital assistant. Computer 81 may comprise CPU 81a, memory 81i, input devices 81b, output devices 81c, power cord 81d, network interface 81h, and one or more storage drives 81g, such as floppy disk drive 81e, CD (or DVD) drive 81f and a hard disk, etc. The input/output devices may include a keyboard, mouse, microphone, track ball, stylus, monitor, printer/plotter, touch screen, speaker, etc., plus the appropriate device drivers and user interface software.

Network interface 81h may be included for connecting to a network 87, which may be any one or a combination of the Internet, an intranet, an extranet, a LAN (local area network), a WAN (wide area network), a wireless network and other networks. Network interface 81h includes the appropriate units for interfacing with the network 87, including, for example, Ethernet card, modem, wireless modem, etc.

Software components may be stored on a floppy disk, CD or another storage medium, and installed on the computer. The software components alternatively (or also) may be communicated through the network interface via a network, such as the Internet, and/or a wireless transmission medium. Further, each software component may comprise one or more segments, subsets of which are retrieved, from the computer hard disk or via the network or transmission medium, as need arises.

The software components in the dental X-ray imaging system may include a graphical user interface to control the hardware, image management functions and interfaces to other dental software packages. The software components also include assorted device drivers, including a wireless communication driver if a wireless interface is provided.

The functions of the system may depend on the hardware and software implementation. The functions may be combined/split or otherwise modified to ease the design, manufacture and serviceability of the system. Thus, image capture control functions may be implemented by, for example, a combination of software and hardware components. The following exemplary image capture functions may be provided: initialize the system, i.e. communicate with the sensor over the USB (or wireless means) and wake it up if required; obtain system status; prepare for exposure by commanding the hardware to enter a wait-for-exposure mode and erase image currently stored in system memory; detect capture of an image, and signal client software that an image has been captured and is ready for upload; initialize image data transfer, and send command to start upload of image data to the system (the image data may be sent as a complete image or streamed as available); a command is sent from client to the system to exit wait-for-exposure mode and enter standby mode; and retrieve integration time.

As shown in FIGS. 2A and 2B, the sensor 13 comprises an array of pixels 14 organized in rows and columns, row and column addressing circuits (not shown) and at least one readout amplifier (also not shown). As part of the image capture function, a number of pixels are designated reference pixels 15. Additional circuitry (not shown) on the chip selects the reference pixels 15 distributed over the chip and compares their signal with a reference level. When a sufficient number of pixels have reached the threshold the image capture starts.

The reference pixels (shaded in the drawings) may be selected either completely randomly distributed over the entire sensor area (as shown, for example, in FIG. 2A) or randomly distributed in selected different rows or columns. Selection of the reference pixels may be performed by software, hardware or a combination.

In one embodiment, as shown in FIG. 2B, two sets of columns are selected as reference pixels. The sets of columns are preferably on opposite sides of the imaging array. An average of the pixel values along a column is taken.

FIG. 3 shows a schematic view of image capture circuitry 30 in an active column sensor, in accordance with a preferred embodiment of the present invention. Note, however, that it would be apparent to one skilled in the art that the present invention may be practiced using other types of X-ray sensors, such as CID, CMOS and other active pixel sensors, having a non-destructive readout capability as well.

The active column sensor has a plurality of columns of pixels, although only the two sets of columns selected as reference pixels are shown in FIG. 3. Each set comprises three columns 31. The means for selecting the reference pixels is not shown in FIG. 3. As suggested above, such means may be hardware circuits, software or a combination, and would be within the knowledge and at the discretion of one skilled in the art.

Preferably all the charge in each of the selected columns is averaged together for one low noise signal 32 per column. Two sets of three columns are logically compared to determine whether at least two out of three columns of summed charges in each set exceeds a predetermined threshold level. Boolean logic units 33 and 34 are used to verify that two out of three columns have exceeded the predetermined threshold level. The Boolean logic units also eliminate (i) any individual pixel defects from lowering device yields and (ii) lower frequency noise sources. Either set of three columns may trigger a counter 35 that then would count down a minimum of 800 milliseconds before causing one frame of video to be read out by block 36. The selected columns of pixels are reset at a 10 Hz frame rate to eliminate any possibility of dark current build up while waiting for an X-ray event.

Because the sensor is randomly accessed, only the pixels that are used for threshold testing (i.e. to determine that an X-ray event occurred) are read out, while the rest of the array is held in reset to eliminate any dark current build-up. Another benefit of random access is that the unused pixels are not clocked and therefore power is conserved. The selected columns are the only pixels that are monitored while waiting for an X-ray event, which allows for a higher than normal frame rate ($\geq 10$ Hz) to monitor and quickly respond to an X-ray event.

Figure 4:
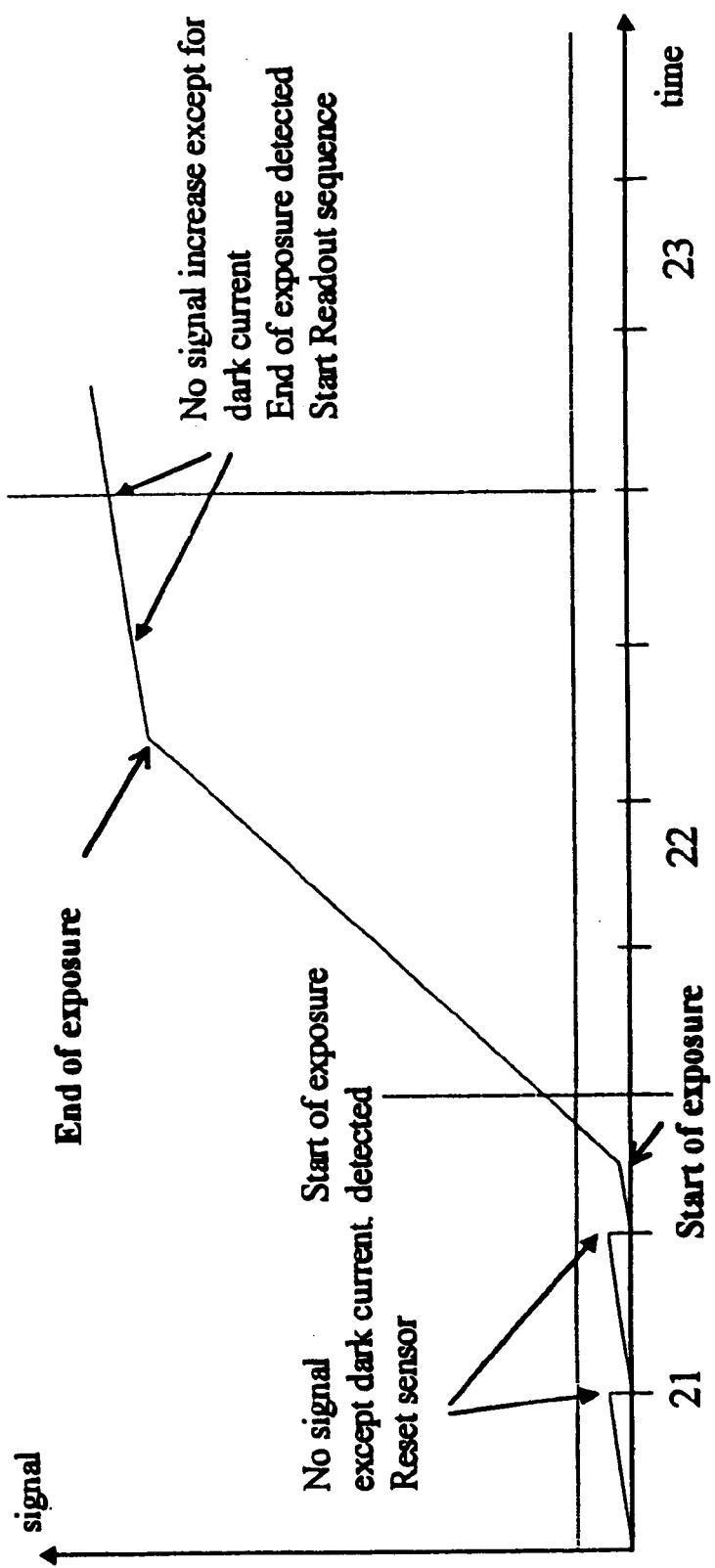
FIG. 4 shows a schematic view of an image capture sequence in accordance with an embodiment of the present invention.

FIG. 4 shows a typical image capture sequence. During the wait for exposure period 21 the signal is monitored and the image sensor is reset at regular intervals. When the signal reaches the threshold level image capture 22 begins. After a specified time interval, or when the signal on the reference pixels is no longer increasing, the image is read out 23.

During "wait for exposure" the reference pixels are compared with the threshold one by one. If, after a predetermined time interval, a predetermined number of reference pixels are above the threshold then a decision is taken that exposure has started. If none or too few of the reference pixels are above the threshold then the entire array is reset and a new scan for reference pixels above the threshold is started. The system then enters "exposure" mode. The threshold on the reference level may be replaced by a circuit monitoring the rate of increase in the signal at the reference pixels. A similar sequence of operation is still required to prevent the pixels from filling by the dark current.

The "end of exposure" condition may be detected in one of two ways. In the simplest configuration a timer is started when the system enters "exposure" mode. That timer is preset to a value which is slightly longer than the longest exposure time used with the system. The "end of exposure" condition is then reached when the timer expires. For applications always using short exposure times this arrangement is sufficient since the extra delay caused by always expecting the maximum exposure time is not noticed by the user and does not cause any significant increase in the parasitic signal caused by the dark current.

The second method to monitor end of exposure is to monitor the increase in signal on the reference pixels. The reference pixels are monitored at regular intervals. As long as the current value of the reference pixel differs from the previous value by an amount which is larger than the increase caused by the dark current then "exposure" mode is maintained. When the signal in the pixel is no longer increasing then "end of exposure" is reached. A typical exposure sequence is as follows:

(1) Reset the sensor to clear all the pixels;

(2) Wait for a specified time interval, such as 100 $\mu$s to 100 ms;

(3) For each reference pixel, read the pixel and compare the signal level of the pixel to a threshold;

(4) If the signal is lower than the threshold, return to step (1);

(5) For each reference pixel, read the pixel again, and compare the current signal level of the pixel to the previous value;

(6) If the value is increasing (at greater than a rate of a dark current), return to step (5);

(7) Wait for at least 20 ms (in the case of an AC X-ray source); and (8) Commence readout or return to step (5).

Figure 5A:
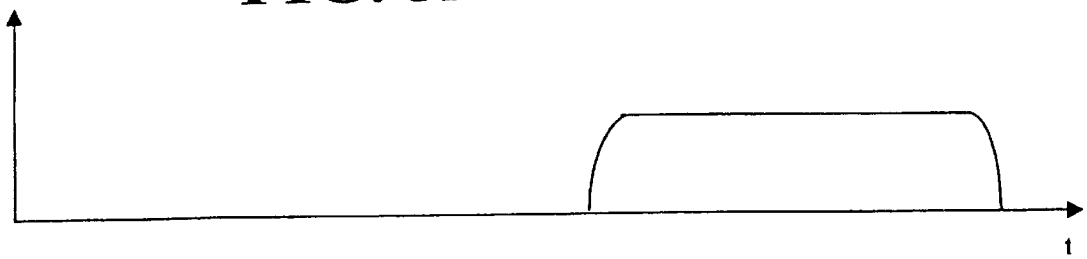
FIGS. 5A through 5C show output characteristics of respective exemplary X-ray sources.
Figure 5B:
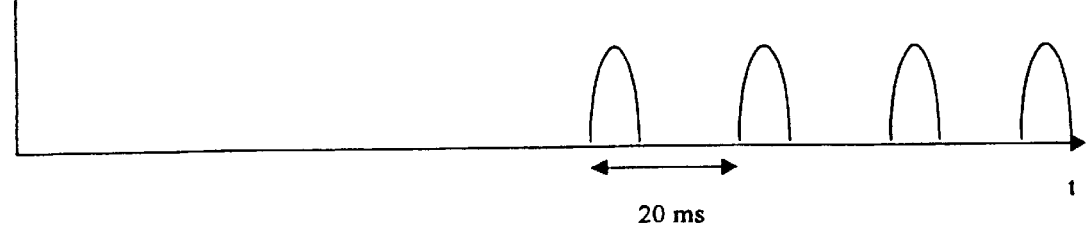
Figure 5C:
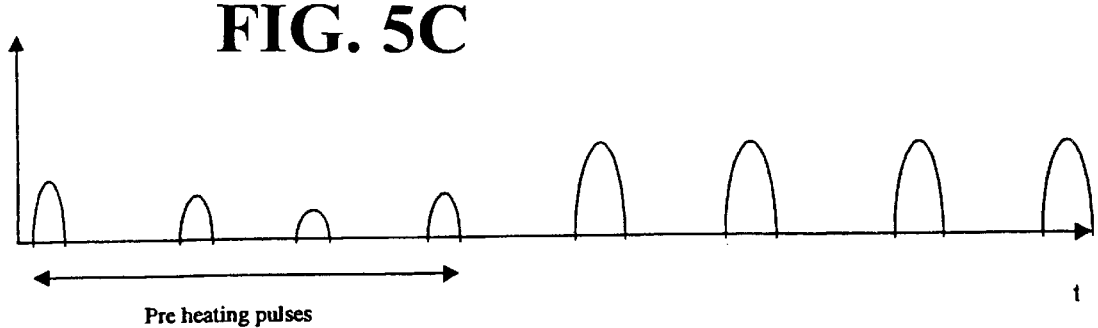

Due to the difference in output characteristics amongst different X-ray generators, as shown for example in FIGS. 5A through 5C, a time delay has to be used [step (7)] before it is determined to be end of exposure.

In a DC-coupled X-ray generator the anode voltage is controlled by a high voltage rectifier, which supplies a constant voltage to the anode of the X-ray tube, as shown in FIG. 5A. The output from the X-ray generator is then a steady flux of X-ray photons from start of exposure to end of exposure.

In AC-coupled X-ray generators the anode current is supplied from a high voltage transformer. The X-ray tube itself acts as a rectifier and outputs a burst of X-ray photons for each half period of the input line frequency (50 Hz in FIG. 5B). Additionally some AC-tubes might also output a couple of weak "pre-heating" pulses before the real exposure begins, as shown in FIG. 5C. The pre-heating pulses are much weaker than the real pulses and can cause a false trigger signal. Any additional pre-heating pulses are then too weak to maintain exposure status.

In order to wait for the real end of exposure a retriggerable timer should be used, which delays the "end of exposure" condition for a specified number of periods of the line frequency. In critical applications, the timer should be software controlled and set to the minimum value required by the specific tube.

The same reference pixels may be used both to detect start of exposure and to detect end of exposure. Alternatively, different reference pixels may be used for. detecting end of exposure. As a third option, different reference pixels may be selected periodically. Further, in the preferred embodiment, the same reference pixels used to test for start of exposure are used as well to test for end of exposure. There is no requirement that this be so. Different reference pixels may be used to test for end of exposure. As noted above, the means for selecting the reference pixels using any of these schemes, regardless of whether it is implemented as hardware circuits, software or a combination, would be within the knowledge and at the discretion of one skilled in the art.

Figure 6:
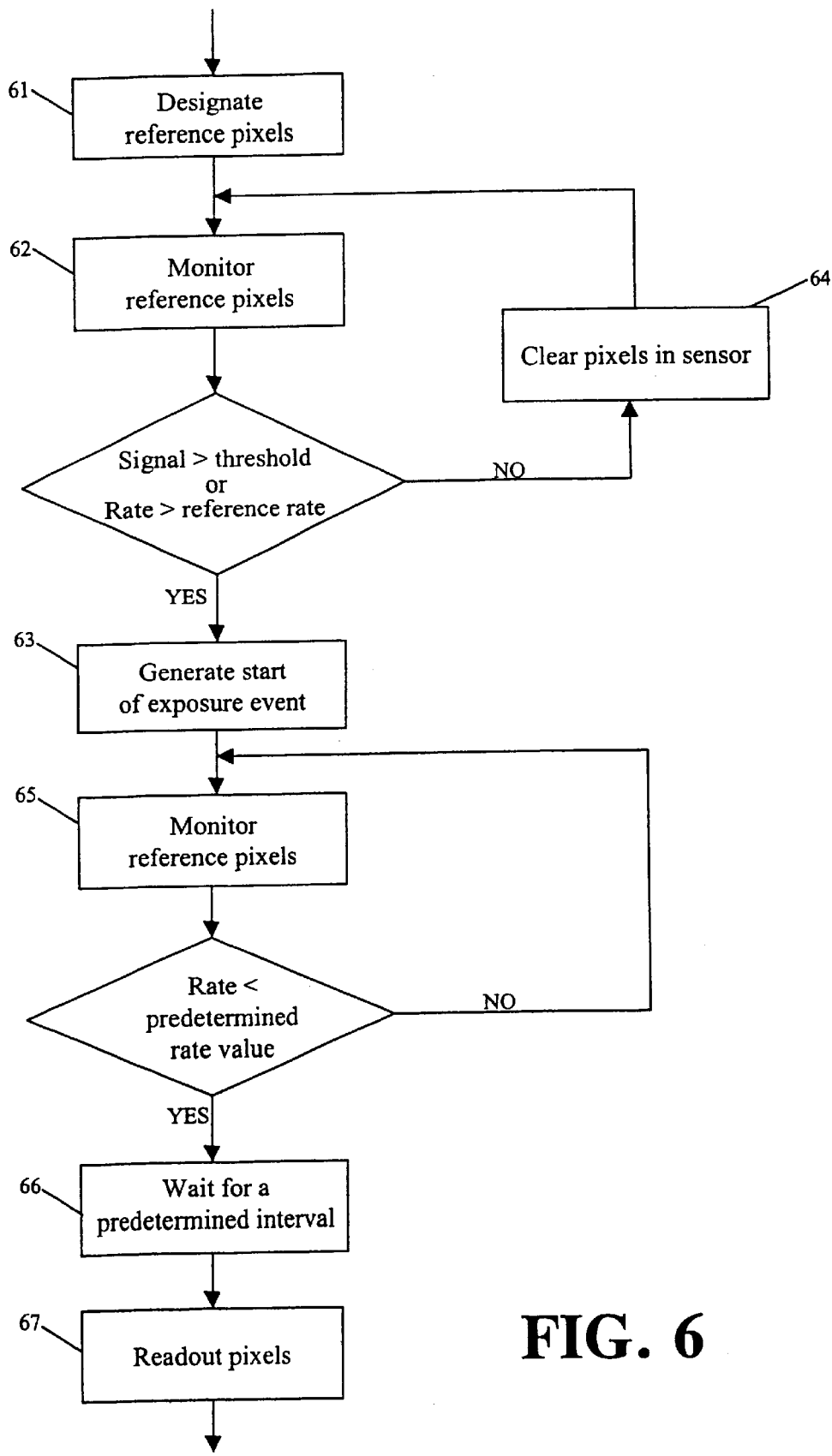
FIG. 6 shows a flow chart of a method in accordance with one embodiment of the present invention.

FIG. 6 shows a flow chart for a method for synchronizing an image capture sequence of an X-ray imaging system with the output from an X-ray source, in accordance with the present invention. The imaging system comprises a solid state radiation detector with a capability of non-destructive readout of pixels arranged in rows and columns.

In step 61, a number of randomly distributed pixels are designated reference pixels. The distribution of pixels may be either totally random or in a limited number of rows or columns. The reference pixels should be well distributed to avoid missed exposures caused by shading of the reference pixels by dense objects. The predetermined reference pixels or pixel like elements may be located in rows or columns distributed in at least two different locations on the sensor. Preferably, a predetermined number of rows or columns located in at least two different areas of the sensor are selected as the reference pixels.

To determine commencement of exposure the reference pixels are continuously monitored for signal in step 62. A signal is integrated over a predetermined time interval at each of the reference pixels. The signal readout from each reference pixel is compared with a predetermined threshold.

If it is determined that the signal level in a minimum number of pixels exceeds a predetermined threshold, a start of exposure event is generated in step 63 and an image capture sequence starts. Otherwise, the entire image sensor is cleared in step 64 and the monitoring for signal continues. The threshold level is set to prevent accidental triggering by dark current at all operating temperatures of interest. The start of exposure event also may be generated when a rate of increase in the signal at the predetermined minimum number of reference pixels exceeds a predetermined reference level.

Following the start of exposure event, change in the accumulated signal at the reference pixels is monitored in step 65. If the X-ray pulse has terminated then the signal no longer changes and readout can be initiated. Thus, if it is determined that a rate of increase in the signal at a predetermined number of reference pixels falls below a predetermined rate value, then, after waiting for a predetermined waiting time interval in step 66, an end of exposure event is generated in step 66. The waiting time interval is set according to a maximum time between pulses in an AC coupled system.

Alternatively, the end of exposure event may be generated a maximum expected exposure time interval after the start of exposure event.

While embodiments of the present invention have been described in detail above, it should be understood that the invention is not limited to the precise embodiments described. Various changes and modifications thereof could be effected by one skilled in the art without departing from the spirit or scope of the invention recited in the appended claims. Improvements and modifications which become apparent to persons of ordinary skill in the art after reading this disclosure, the drawings and the appended claims are deemed within the spirit and scope of the present invention.

What is claimed is:

1. An X-ray imaging system comprising:

an X-ray image sensor including a plurality of CMOS active column sensor elements; and an image capture controller which communicates with the X-ray image sensor to read out pixel values from selected ones of the plurality of CMOS active column sensor elements of the X-ray image sensor.

2. The X-ray imaging system of claim 1, wherein the X-ray imaging system is used as a dental X-ray imaging system.

3. The X-ray imaging system of claim 1, wherein the image capture controller randomly selects reference pixels from the plurality of CMOS active column sensor elements, and compares a signal of the reference pixels to a predetermined level to determine a start of X-ray exposure.

4. The X-ray imaging system of claim 3, wherein the image capture controller randomly selects second reference pixels from the plurality of CMOS active column sensor elements, and monitors the second reference pixels to determine an end of X-ray exposure.

5. The X-ray imaging system of claim 1, wherein the X-ray image sensor is an intra-oral sensor.

6. The X-ray imaging system of claim 1 further comprising a wireless interface for coupling the X-ray image sensor to the image capture controller.

7. An intraoral X-ray image sensing system comprising:

a scintillator that converts an X-ray energy image into a visible-light image; and a sensor array including a plurality of CMOS active column sensors, said sensor array converting the visible-light image an electrical signal.

8. The intraoral X-ray image sensing system of claim 7, further comprising
an image capture controller,
wherein the image capture controller randomly selects reference pixels from the plurality of CMOS active column sensors, controls readout of pixel values from the selected reference pixels, and compares a signal of the reference pixels to a predetermined level to determine a start of X-ray exposure.

9. The intraoral X-ray image sensing system of claim 8, wherein the image capture controller randomly selects second reference pixels from the plurality of CMOS active column sensors, and monitors the second reference pixels to determine an end of X-ray exposure.

10. The intraoral X-ray image sensing system of claim 7, further comprising
an image capture controller,
wherein the scintillator, the sensor array and the image capture controller are integrated in a sensor assembly, and the image capture controller controls readout of pixel values from selected ones of the plurality of CMOS active column sensors.

11. An X-ray imaging system comprising:
an X-ray image sensor including a plurality of sensor elements; and
an image capture controller,
wherein the image capture controller communicates with the X-ray image sensor to read out pixel values from selected ones of the plurality of sensor elements, randomly selects reference pixels from the plurality of sensor elements, and compares a signal of the reference pixels to a predetermined level to determine a start of X-ray exposure.

12. The X-ray imaging system of claim 11, wherein the image capture controller and the X-ray image sensor are integrated in a sensor assembly.

13. The X-ray imaging system of claim 11, wherein the image capture controller randomly selects second reference pixels from the plurality of sensor elements, and monitors the second reference pixels to determine an end of X-ray exposure.

14. The X-ray imaging system of claim 11, further comprising a wireless interface for coupling the X-ray image sensor to the image capture controller.

15. The X-ray imaging system of claim 11, wherein the X-ray imaging system is used as a dental X-ray imaging system.

16. The X-ray imaging system of claim 11, wherein the X-ray image sensor is an intra-oral sensor.

* * * * *